(12) United States Patent
Bacon

(10) Patent No.: US 9,707,360 B2
(45) Date of Patent: Jul. 18, 2017

(54) SUBSTANCE SOURCE

(71) Applicant: CLINICAL DESIGNS LIMITED, Petersfield, Hampshire (GB)

(72) Inventor: Raymond Bacon, Petersfield (GB)

(73) Assignee: CLINICAL DESIGNS LIMITED, Petersfield, Hampshire (GB)

(*) Notice: Subject to any disclaimer, the term of this patent is extended or adjusted under 35 U.S.C. 154(b) by 134 days.

(21) Appl. No.: 14/624,927

(22) Filed: Feb. 18, 2015

(65) Prior Publication Data
US 2015/0157814 A1  Jun. 11, 2015

Related U.S. Application Data

(62) Division of application No. 11/667,957, filed as application No. PCT/GB2005/004430 on Nov. 17, 2005, now abandoned.

(30) Foreign Application Priority Data

Nov. 19, 2004 (GB) .................. 0425518.8

(51) Int. Cl.
*A61M 15/00* (2006.01)
*G06M 1/08* (2006.01)
(Continued)

(52) U.S. Cl.
CPC ...... *A61M 15/0076* (2014.02); *A61M 15/008* (2014.02); *A61M 15/009* (2013.01);
(Continued)

(58) Field of Classification Search
CPC ........ A61M 2202/04; A61M 2205/123; A61M 2202/02; A61M 15/009; A61M 15/0075;
(Continued)

(56) References Cited

U.S. PATENT DOCUMENTS 2,002,835 A   5/1935  Rose
2,716,013 A   8/1955  Tinker
(Continued)

FOREIGN PATENT DOCUMENTS

AU      776816       7/2002
AU      2003234746   9/2003
(Continued)

OTHER PUBLICATIONS

Israeli associate letter dated Jan. 3, 2012, reporting Office Action issued in Israeli Application No. 183231 citing GB 2381201.
(Continued)

*Primary Examiner* — Paul R Durand
*Assistant Examiner* — Robert Nichols, II
(74) *Attorney, Agent, or Firm* — Nixon & Vanderhye P.C.

(57) ABSTRACT

A source of gaseous, gas borne or droplet substance having: an inner pressurized container (1), a substance-release valve (2) device sealed across an end of the container (1), a spout (4) displaceable inwards of the container (1) against a spring of the valve (2) device for substance release; the source also includes: an outer enclosure enclosing the inner container along its length (12), at least partially its end (14) remote from the spout (4) and partially at its spout end (19), the outer enclosure and the inner container (1) being arranged to react force for displacement of the spout (4) on substance release; a counter (20) accommodated within the outer enclosure for counting substance release displacements of the spout (4); and a window (22) in the outer enclosure for viewing the count of the counter (20).

14 Claims, 12 Drawing Sheets

(51) Int. Cl.
  *G06M 1/22* (2006.01)
  *G06M 1/04* (2006.01)
  *A61M 16/12* (2006.01)
  *A61M 16/20* (2006.01)

(52) U.S. Cl.
  CPC .... *A61M 15/0021* (2014.02); *A61M 15/0025* (2014.02); *A61M 15/0073* (2014.02); *A61M 15/0075* (2014.02); *A61M 16/12* (2013.01); *A61M 16/20* (2013.01); *G06M 1/041* (2013.01); *G06M 1/045* (2013.01); *G06M 1/083* (2013.01); *G06M 1/22* (2013.01); *A61M 2202/02* (2013.01); *A61M 2202/04* (2013.01); *A61M 2205/123* (2013.01)

(58) Field of Classification Search
  CPC ............ A61M 15/008; A61M 15/0073; A61M 16/20; A61M 15/0021; A61M 15/0076; A61M 15/0071; G06M 1/22; G06M 1/083; G06M 1/041; G06M 1/045
  USPC ....... 222/36, 38; 128/200.12, 200.23, 200.14
  See application file for complete search history.

(56) References Cited

U.S. PATENT DOCUMENTS

| | | |
|---|---|---|
| 2,922,613 A | 6/1960 | Beecham |
| 3,103,335 A | 9/1963 | Martinez |
| 3,184,115 A | 5/1965 | Meshberg |
| 3,190,497 A | 6/1965 | Anthon |
| 3,329,389 A | 7/1967 | Clark |
| 3,598,288 A | 8/1971 | Posgate |
| 3,610,480 A | 10/1971 | Lipfert et al. |
| 3,746,196 A | 7/1973 | Sako |
| 4,142,651 A | 3/1979 | Leopoldi |
| 4,361,148 A | 11/1982 | Shackleford |
| 4,576,157 A | 3/1986 | Raghuprasad |
| 4,664,107 A | 5/1987 | Wass |
| 4,753,371 A | 6/1988 | Michielin |
| 4,817,822 A | 4/1989 | Rand |
| 4,955,371 A | 9/1990 | Zamba |
| 4,984,158 A | 1/1991 | Hillsman |
| 5,020,527 A | 6/1991 | Dessertine |
| 5,031,610 A | 7/1991 | Armstrong |
| 5,042,685 A | 8/1991 | Moulding, Jr. |
| 5,069,204 A | 12/1991 | Smith |
| 5,119,806 A | 6/1992 | Palson |
| 5,152,456 A | 10/1992 | Ross |
| 5,184,761 A | 2/1993 | Lee |
| 5,193,745 A | 3/1993 | Holm |
| 5,217,004 A | 6/1993 | Blasnik |
| 5,239,992 A | 8/1993 | Bougamont |
| 5,261,601 A | 11/1993 | Ross |
| 5,273,172 A | 12/1993 | Rossbach |
| 5,295,479 A | 3/1994 | Lankinen |
| 5,299,701 A | 4/1994 | Barker |
| 5,347,998 A | 9/1994 | Hodson |
| 5,388,572 A | 2/1995 | Mulhauser |
| 5,408,994 A | 4/1995 | Wass |
| 5,411,173 A | 5/1995 | Weinstein |
| 5,415,161 A | 5/1995 | Ryder |
| 5,421,482 A | 6/1995 | Garby |
| 5,482,030 A | 1/1996 | Klein |
| 5,487,378 A | 1/1996 | Robertson |
| 5,501,375 A | 3/1996 | Nilson |
| 5,505,192 A | 4/1996 | Samiotes et al. |
| 5,511,540 A | 4/1996 | Bryant |
| 5,544,647 A | 8/1996 | Jewett |
| 5,544,657 A | 8/1996 | Kurowski |
| 5,546,932 A | 8/1996 | Galli |
| 5,549,101 A | 8/1996 | Trofast |
| 5,549,226 A | 8/1996 | Kopp |
| 5,564,414 A | 10/1996 | Walker |
| 5,611,444 A | 3/1997 | Garby |
| 5,622,163 A | 4/1997 | Jewett |
| 5,623,920 A | 4/1997 | Bryant |
| 5,645,050 A | 7/1997 | Zlerenberg |
| 5,682,875 A | 11/1997 | Blower |
| 5,692,492 A | 12/1997 | Bruna |
| 5,718,355 A | 2/1998 | Garby |
| 5,772,085 A | 6/1998 | Bryant |
| 5,794,612 A | 8/1998 | Wachter |
| 5,809,997 A | 9/1998 | Wolf |
| 5,839,429 A | 11/1998 | Marnfeldt |
| 5,878,917 A | 3/1999 | Reinhard |
| 5,904,139 A | 5/1999 | Hauser |
| 5,960,609 A | 10/1999 | Abrams |
| 5,988,496 A | 11/1999 | Bruna |
| 5,996,577 A | 12/1999 | Ohki |
| 6,006,745 A | 12/1999 | Marecki |
| 6,014,970 A | 1/2000 | Ivri |
| 6,085,742 A | 7/2000 | Wachter |
| 6,142,146 A | 11/2000 | Abrams |
| 6,148,815 A | 11/2000 | Wolf |
| 6,149,054 A | 11/2000 | Cirrillo |
| 6,152,130 A | 11/2000 | Abrams |
| 6,164,494 A | 12/2000 | Marelli |
| 6,196,218 B1 | 3/2001 | Voges |
| 6,202,642 B1 | 3/2001 | McKinnon |
| 6,234,168 B1 | 5/2001 | Bruna |
| 6,240,918 B1 | 6/2001 | Ambrosio |
| 6,253,762 B1 | 7/2001 | Britto |
| 6,260,549 B1 | 7/2001 | Sosiak |
| 6,283,365 B1 | 9/2001 | Bason |
| 6,318,361 B1 | 11/2001 | Sosiak |
| 6,325,062 B1 | 12/2001 | Sosiak |
| 6,336,453 B1 | 1/2002 | Scarrott |
| 6,354,290 B1 | 3/2002 | Howlett |
| 6,357,442 B1 | 3/2002 | Casper |
| 6,360,739 B1 | 3/2002 | Rand |
| 6,397,839 B1 | 6/2002 | Stradella |
| 6,405,727 B1 | 6/2002 | MacMichael et al. |
| 6,415,784 B1 | 7/2002 | Christup |
| 6,422,234 B1 | 7/2002 | Bacon |
| 6,425,392 B1 | 7/2002 | Sosiak |
| 6,427,683 B1 | 8/2002 | Drachmann |
| 6,431,168 B1 | 8/2002 | Rand |
| 6,435,372 B1 | 8/2002 | Blacker |
| 6,439,227 B1 | 8/2002 | Myrman |
| 6,443,146 B1 | 9/2002 | Voges |
| 6,446,627 B1 | 9/2002 | Bowman |
| 6,460,537 B1 | 10/2002 | Bryant |
| 6,470,884 B2 | 10/2002 | Horlin |
| 6,474,331 B1 | 11/2002 | Rand |
| 6,510,847 B1 | 1/2003 | Helgesson |
| 6,516,799 B1 | 2/2003 | Greenwood |
| 6,546,928 B1 | 4/2003 | Ashurst |
| 6,553,988 B1 | 4/2003 | Holroyd |
| 6,581,590 B1 | 6/2003 | Genova |
| 6,596,260 B1 | 7/2003 | Brugger |
| 6,601,582 B2 | 8/2003 | Rand |
| 6,615,827 B2 | 9/2003 | Greenwood |
| 6,651,844 B2 | 11/2003 | Tomaka et al. |
| 6,655,371 B2 | 12/2003 | Gallops |
| 6,655,379 B2 | 12/2003 | Clark |
| 6,659,307 B1 | 12/2003 | Stradella |
| 6,672,304 B1 | 1/2004 | Casper |
| 6,729,330 B2 | 5/2004 | Scarrott |
| 6,745,761 B2 | 6/2004 | Christrup |
| 6,752,145 B1 | 6/2004 | Bonney |
| 6,752,153 B1 | 6/2004 | Eckert |
| 6,755,190 B2 | 6/2004 | Rasmussen |
| 6,759,108 B1 | 7/2004 | Ota |
| 6,766,220 B2 | 7/2004 | McRae |
| 6,805,116 B2 | 10/2004 | Hodson |
| 6,823,863 B2 | 11/2004 | Huxham et al. |
| 6,860,262 B2 | 3/2005 | Christrup |
| 6,866,037 B1 | 3/2005 | Aslin |
| 6,866,038 B2 | 3/2005 | Bacon |
| 6,889,687 B1 | 5/2005 | Olsson |
| 6,907,876 B1 | 6/2005 | Clark |
| 6,926,002 B2 | 8/2005 | Scarrott |
| 7,007,689 B2 | 3/2006 | Burns |

(56) References Cited

U.S. PATENT DOCUMENTS

| | | |
|---|---|---|
| 7,036,505 B2 | 5/2006 | Bacon |
| 7,047,964 B2 | 5/2006 | Bacon |
| 7,047,967 B2 | 5/2006 | Knudsen |
| 7,072,738 B2 | 7/2006 | Bonney |
| 7,093,594 B2 | 8/2006 | Harrison |
| 7,100,530 B2 | 9/2006 | Lu |
| 7,107,986 B2 | 9/2006 | Rand |
| 7,147,170 B2 | 12/2006 | Nguyen |
| 7,167,776 B2 | 1/2007 | Maharajh |
| 7,191,918 B2 | 3/2007 | Ouyang |
| 7,195,134 B2 | 3/2007 | Ouyang |
| 7,219,664 B2 | 5/2007 | Ruckdeschel |
| 7,225,805 B2 | 6/2007 | Bacon |
| 7,234,460 B2 | 6/2007 | Greenleaf |
| 7,237,727 B2 | 7/2007 | Wang |
| 7,270,124 B2 | 9/2007 | Rasmussen |
| 7,275,660 B2 | 10/2007 | Stradella |
| 7,296,567 B2 | 11/2007 | Mahon |
| 7,299,800 B2 | 11/2007 | Stradella |
| 7,299,801 B2 | 11/2007 | Hodson |
| 7,306,116 B2 | 12/2007 | Fuchs |
| 7,318,434 B2 | 1/2008 | Gumaste |
| 7,322,352 B2 | 1/2008 | Minshull |
| 7,331,340 B2 | 2/2008 | Barney |
| 7,334,577 B2 | 2/2008 | Gumaste |
| 7,341,057 B2 | 3/2008 | Scarrott |
| 7,347,200 B2 | 3/2008 | Jones |
| 7,347,202 B2 | 3/2008 | Aslin |
| 7,367,333 B2 | 5/2008 | Hodson |
| 7,387,121 B2 | 6/2008 | Harvey |
| 7,400,940 B2 | 7/2008 | McRae |
| 7,418,961 B2 | 9/2008 | Jones |
| 7,448,342 B2 | 11/2008 | von Schuckmann |
| 7,454,267 B2 | 11/2008 | Bonney |
| 7,464,708 B2 | 12/2008 | Marx |
| 7,497,214 B2 | 3/2009 | Hodson |
| 7,510,100 B2 | 3/2009 | Stradella |
| 7,597,099 B2 | 10/2009 | Jones |
| 7,621,273 B2 | 11/2009 | Morton et al. |
| 7,637,260 B2 | 12/2009 | Holroyd |
| 7,743,765 B2 | 6/2010 | Hodson |
| 2001/0013342 A1 | 8/2001 | Burns |
| 2001/0013343 A1 | 8/2001 | Andersson |
| 2001/0025639 A1 | 10/2001 | Christrup |
| 2001/0032644 A1 | 10/2001 | Hodson |
| 2002/0000225 A1 | 1/2002 | Schuler |
| 2002/0011247 A1 | 1/2002 | Ivri |
| 2002/0026938 A1 | 3/2002 | Hodson |
| 2002/0043262 A1 | 4/2002 | Langford |
| 2002/0088458 A1 | 7/2002 | Christrup |
| 2002/0100473 A1 | 8/2002 | Christrup |
| 2002/0104530 A1 | 8/2002 | Ivri |
| 2002/0104532 A1 | 8/2002 | Christrup |
| 2002/0139812 A1 | 10/2002 | Scarrott |
| 2002/0189611 A1 | 12/2002 | Greenwood |
| 2003/0033055 A1 | 2/2003 | McRae |
| 2003/0089368 A1 | 5/2003 | Zhao |
| 2003/0106550 A1 | 6/2003 | Harvey |
| 2003/0116155 A1 | 6/2003 | Rasmussen |
| 2003/0136401 A1 | 7/2003 | Jansen |
| 2003/0138559 A1 | 7/2003 | Ashurst |
| 2003/0150448 A1 | 8/2003 | Bacon |
| 2003/0178021 A1 | 9/2003 | Rasmussen |
| 2003/0183225 A1 | 10/2003 | Knudsen |
| 2003/0183226 A1 | 10/2003 | Brand |
| 2003/0192535 A1 | 10/2003 | Christrup |
| 2003/0207057 A1 | 11/2003 | Britto |
| 2003/0230305 A1 | 12/2003 | Christrup |
| 2004/0005475 A1 | 1/2004 | Curie |
| 2004/0020486 A1 | 2/2004 | Huxham et al. |
| 2004/0025867 A1 | 2/2004 | Holroyd |
| 2004/0025868 A1 | 2/2004 | Bruna |
| 2004/0025870 A1 | 2/2004 | Harrison |
| 2004/0055596 A1 | 3/2004 | Bacon |
| 2004/0065320 A1 | 4/2004 | Bacon |
| 2004/0065326 A1 | 4/2004 | MacMichael et al. |
| 2004/0069301 A1 | 4/2004 | Bacon |
| 2004/0079362 A1 | 4/2004 | Christrup |
| 2004/0089299 A1 | 5/2004 | Bonney |
| 2004/0107962 A1 | 6/2004 | Harrison |
| 2004/0129793 A1 | 7/2004 | Nguyen |
| 2004/0134488 A1 | 7/2004 | Davies |
| 2004/0134489 A1 | 7/2004 | Burns |
| 2004/0139965 A1 | 7/2004 | Greenleaf |
| 2004/0139966 A1 | 7/2004 | Hodson |
| 2004/0144798 A1 | 7/2004 | Ouyang |
| 2004/0149773 A1 | 8/2004 | Ouyang |
| 2004/0172162 A1 | 9/2004 | Bonney |
| 2004/0187865 A1 | 9/2004 | Ashurst |
| 2004/0221840 A1 | 11/2004 | Stockman-Lamb |
| 2005/0011515 A1 | 1/2005 | Lee et al. |
| 2005/0016528 A1 | 1/2005 | Aslin |
| 2005/0076904 A1 | 4/2005 | Jones |
| 2005/0081846 A1 | 4/2005 | Barney |
| 2005/0087191 A1 | 4/2005 | Morton |
| 2005/0121024 A1 | 6/2005 | Langford |
| 2005/0126469 A1 | 6/2005 | Lu |
| 2005/0143866 A1 | 6/2005 | McRae |
| 2005/0183724 A1 | 8/2005 | Gumaste |
| 2005/0205512 A1 | 9/2005 | Scarrott |
| 2005/0209558 A1 | 9/2005 | Marx |
| 2005/0263612 A1 | 12/2005 | Wang |
| 2006/0011197 A1 | 1/2006 | Hodson |
| 2006/0037611 A1 | 2/2006 | Mahon |
| 2006/0047368 A1 | 3/2006 | Maharajh |
| 2006/0060192 A1 | 3/2006 | Lu |
| 2006/0071027 A1 | 4/2006 | Davies |
| 2006/0131346 A1 | 6/2006 | Purkins |
| 2006/0151524 A1 | 7/2006 | Stradella |
| 2006/0163275 A1 | 7/2006 | Stradella |
| 2006/0174869 A1 | 8/2006 | Gumaste |
| 2006/0186223 A1 | 8/2006 | Wang |
| 2006/0213505 A1 | 9/2006 | Hodson |
| 2006/0213506 A1 | 9/2006 | Hodson |
| 2006/0213510 A1 | 9/2006 | Hodson |
| 2006/0231093 A1 | 10/2006 | Burge |
| 2006/0237002 A1 | 10/2006 | Bonney |
| 2006/0237009 A1 | 10/2006 | Jones |
| 2006/0243275 A1 | 11/2006 | Ruckdeschel |
| 2006/0254581 A1 | 11/2006 | Genova |
| 2006/0278225 A1 | 12/2006 | MacMichael et al. |
| 2006/0283444 A1 | 12/2006 | Jones |
| 2006/0289005 A1 | 12/2006 | Jones |
| 2006/0289008 A1 | 12/2006 | Rand |
| 2007/0017506 A1 | 1/2007 | Bell et al. |
| 2007/0017511 A1 | 1/2007 | Ohki |
| 2007/0029341 A1 | 2/2007 | Stradella |
| 2007/0051745 A1 | 3/2007 | Poulard |
| 2007/0056502 A1 | 3/2007 | Lu |
| 2007/0056580 A1 | 3/2007 | Jones |
| 2007/0056585 A1 | 3/2007 | Davies |
| 2007/0062518 A1 | 3/2007 | Geser |
| 2007/0062522 A1 | 3/2007 | Bacon |
| 2007/0089735 A1 | 4/2007 | Langford |
| 2007/0119450 A1 | 5/2007 | Wharton |
| 2007/0144514 A1 | 6/2007 | Yeates |
| 2007/0163576 A1 | 7/2007 | Bacon |
| 2007/0181120 A1 | 8/2007 | Wright |
| 2007/0181123 A1 | 8/2007 | Houzego |
| 2007/0194041 A1 | 8/2007 | Stradella |
| 2007/0210102 A1 | 9/2007 | Stradella |
| 2007/0241136 A1 | 10/2007 | Poulard |
| 2007/0246042 A1 | 10/2007 | Perkins |
| 2007/0251950 A1 | 11/2007 | Bacon |
| 2007/0284383 A1 | 12/2007 | Wright |
| 2008/0017189 A1 | 1/2008 | Ruckdeschel |
| 2008/0017193 A1 | 1/2008 | Jones |
| 2008/0035144 A1 | 2/2008 | Bowman |
| 2008/0041877 A1 | 2/2008 | Stradella |
| 2008/0047556 A1 | 2/2008 | Hodson |
| 2008/0060643 A1 | 3/2008 | Hodson |
| 2008/0066742 A1 | 3/2008 | Hodson |
| 2008/0092887 A1 | 4/2008 | Hodson |
| 2008/0107848 A1 | 5/2008 | Bacon |

(56) References Cited

U.S. PATENT DOCUMENTS

| | | |
|---|---|---|
| 2008/0115784 A1 | 5/2008 | Gumaste |
| 2008/0135575 A1 | 6/2008 | Ingram |
| 2008/0135576 A1 | 6/2008 | Bacon |
| 2008/0173301 A1 | 7/2008 | Deaton |
| 2008/0210224 A1 | 9/2008 | Brunnberg |
| 2008/0210226 A1 | 9/2008 | Butterworth |
| 2008/0251004 A1 | 10/2008 | Stradella |
| 2008/0283541 A1 | 11/2008 | Warby |
| 2008/0314383 A1 | 12/2008 | Barney |
| 2009/0114219 A1 | 5/2009 | Ferris |
| 2009/0211578 A1 | 8/2009 | Fletcher |
| 2009/0229604 A1 | 9/2009 | Pearson |
| 2009/0229607 A1 | 9/2009 | Brunnberg |
| 2009/0293870 A1 | 12/2009 | Brunnberg |
| 2009/0308385 A1 | 12/2009 | Brewer |
| 2009/0308389 A1 | 12/2009 | Pocock |
| 2010/0012115 A1 | 1/2010 | Bacon |
| 2010/0065050 A1 | 3/2010 | Holroyd |

FOREIGN PATENT DOCUMENTS

| | | |
|---|---|---|
| AU | 2003234748 | 9/2003 |
| CN | 1 079 167 | 12/1993 |
| DE | 629163 | 4/1936 |
| DE | 1077932 | 3/1960 |
| DE | 8715223 U | 2/1988 |
| DE | 4111895 | 10/1992 |
| DE | 19745513 | 4/1999 |
| DE | 29818662 U | 3/2000 |
| DE | 10061723 C | 7/2002 |
| DE | 202004021188 U | 3/2007 |
| EP | 0428380 B | 5/1991 |
| EP | 0501365 | 9/1992 |
| EP | 0629563 A | 12/1994 |
| EP | 0 775 499 | 5/1997 |
| EP | 1003583 B | 5/2000 |
| EP | 1019125 B | 7/2000 |
| EP | 1229953 B | 8/2002 |
| EP | 1443997 B | 8/2004 |
| EP | 1 475 116 A2 | 11/2004 |
| EP | 0883415 B | 12/2008 |
| FR | 2654627 | 5/1991 |
| FR | 2660630 | 10/1991 |
| FR | 2701653 | 8/1994 |
| GB | 161969 | 7/1922 |
| GB | 939324 | 10/1963 |
| GB | 1026763 | 4/1966 |
| GB | 1270272 | 4/1972 |
| GB | 2195544 | 4/1988 |
| GB | 2262452 A | 6/1993 |
| GB | 2263873 | 8/1993 |
| GB | 2264238 A | 8/1993 |
| GB | 2266466 A | 11/1993 |
| GB | 2279571 A | 1/1995 |
| GB | 2279879 B | 1/1995 |
| GB | 2292891 A | 3/1996 |
| GB | 2 320 489 | 6/1998 |
| GB | 2366519 B | 3/2002 |
| GB | 2 372 542 | 8/2002 |
| GB | 2372542 | 8/2002 |
| GB | 2 385 640 | 8/2003 |
| GB | 2398250 A | 8/2004 |
| GB | 2398251 A | 8/2004 |
| GB | 0425518.8 | 11/2004 |
| GB | 2 381 201 | 2/2005 |
| GB | 2429166 A | 2/2007 |
| JP | 63251880 | 10/1988 |
| JP | 9-168593 | 6/1997 |
| JP | 2003-56254 | 2/2003 |
| JP | 2003-508166 | 3/2003 |
| WO | WO 92/07599 | 5/1992 |
| WO | WO 92/07600 | 5/1992 |
| WO | WO 93/03783 | 3/1993 |
| WO | 93/24167 | 12/1993 |
| WO | WO 93/24167 | 12/1993 |
| WO | WO 94/05359 | 3/1994 |
| WO | WO 94/19042 | 9/1994 |
| WO | WO 95/08484 | 3/1995 |
| WO | WO 96/39337 | 12/1996 |
| WO | WO 97/11296 | 3/1997 |
| WO | WO 99/36116 | 7/1999 |
| WO | WO 00/59806 | 10/2000 |
| WO | WO 01/31578 | 5/2001 |
| WO | WO 01/37909 | 5/2001 |
| WO | WO 02/11802 A2 | 2/2002 |
| WO | WO 02/38207 | 5/2002 |
| WO | WO 02/43794 | 6/2002 |
| WO | WO 02/058771 A1 | 8/2002 |
| WO | WO 03/101514 | 12/2003 |
| WO | WO 2004/041339 A2 | 5/2004 |
| WO | WO 2004/089451 | 10/2004 |
| WO | WO 2004/096329 | 11/2004 |
| WO | WO 2006/062449 | 6/2006 |
| WO | WO 2006/119766 | 11/2006 |
| WO | WO 2007/012854 | 2/2007 |
| WO | WO 2007/066140 | 6/2007 |
| WO | WO 2007/077450 | 7/2007 |
| WO | WO 2007/141520 | 12/2007 |
| WO | WO 2008/025087 | 3/2008 |
| WO | WO 2008/040772 | 4/2008 |
| WO | WO 2008/079350 | 7/2008 |
| WO | WO 2008/079360 | 7/2008 |
| WO | WO 2008/087369 | 7/2008 |
| WO | WO 2008/104366 | 9/2008 |
| WO | WO 2008/119552 | 10/2008 |
| WO | WO 2008/148864 | 12/2008 |

OTHER PUBLICATIONS

International Search Report of PCT/GB2005/004430, mailed Apr. 18, 2006.

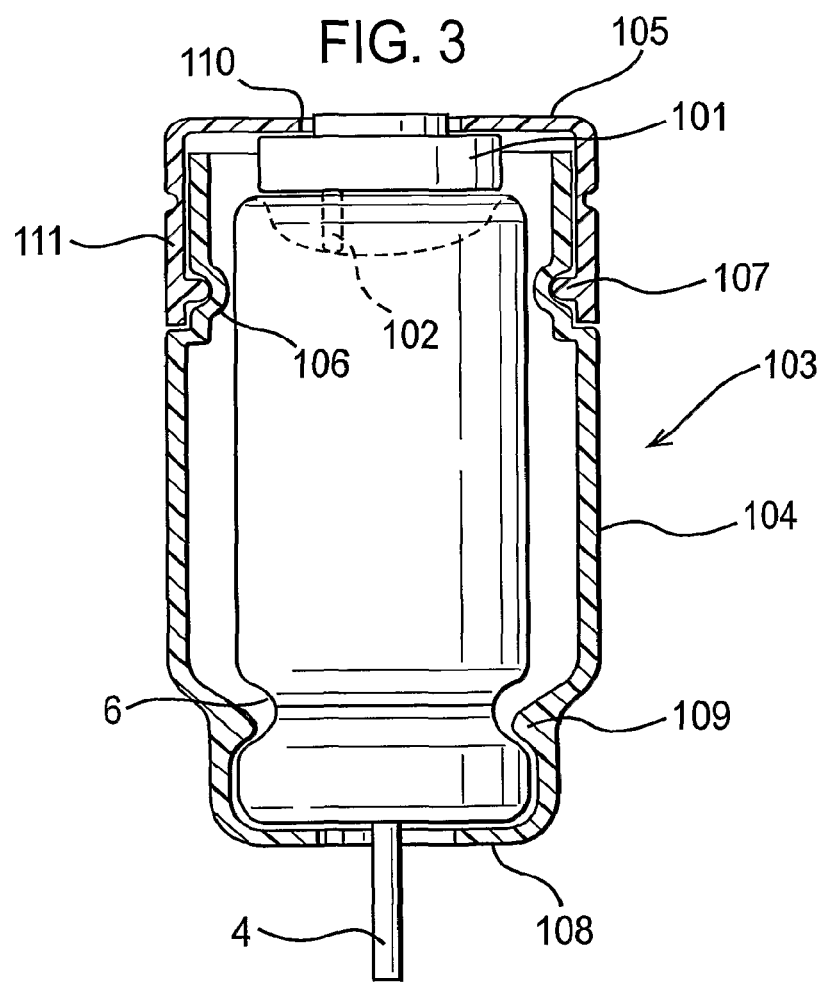
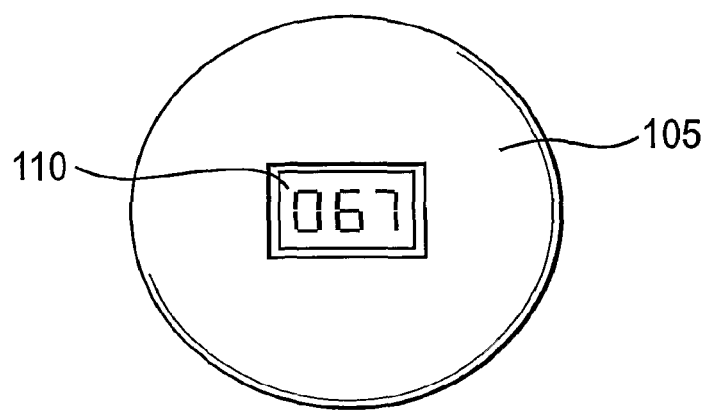

SUBSTANCE SOURCE

This application is a divisional of U.S. application Ser. No. 11/667,957 (published as US 2008-0135576 A1), filed May 17, 2007 (abandoned), which is a U.S. national phase of International Application PCT/GB2005/004430, filed 17 Nov. 2005, which designated the U.S. and claims priority of GB 0425518.8, filed 19 Nov. 2004, the entire contents of each of which are hereby incorporated by reference.

BACKGROUND OF THE INVENTION

The present invention relates to provided a source of a gaseous, gas borne or droplet substance.

Such sources are used for dispensing medicaments in metered doses via a dispenser. There is an increasing desire for the number of doses dispensed and/or left in the source to be counted, so that a user can know the number of doses remaining before a fresh source (and dispenser) is required.

The object of the present invention is to provide a substance source with an integral counter.

The Invention

According to a first aspect of the invention there is provided a source of a gaseous, gas borne or droplet substance having:
an inner pressurised container,
a substance-release valve device sealed across an end of the container,
a spout displaceable inwards of the container against a spring of the valve device for substance release,
the source also including:
an outer enclosure enclosing the inner container along its length, at least partially across its end remote from the spout and partially at its spout end,
the outer enclosure and the inner container being arranged to react force for displacement of the spout on substance release;
a counter accommodated within the outer enclosure for counting substance release displacements of the spout; and
a window in the outer enclosure for viewing the count of the counter.30

In certain embodiments, the counter is arranged at the end of the outer enclosure, for reacting and counting occurrences of spout-displacement force from the inner container to the outer enclosure. In particular where the substance is a high value medicament, the counter can be a single use electronic counter. However, since an electronic counter is a relatively expensive component of a medicament source, in the preferred embodiment with such a counter, it can be a multi-use electronic counter, with the outer enclosure being provided with a frangible enclosure for the counter, whereby the counter can be removed from the medicament source by breaking the enclosure when it is has reached its normal dose count limit, reset and installed on a fresh source using its fresh frangible closure. In this case, the counter provides the sole abutment for the inner container as regards spout-displacement force, whereby residual medicament cannot be used once the counter has been removed.

Again, the counter can be a removable or an irremovable mechanical counter. The mechanical counter can include a dual set of ratchet teeth and pawls, with angular incrementation determined by the ratchet teeth and can be housed within the outer enclosure and gearing is provided between an incremented ratchet disc and an indicator disc viewable through the window in the outer enclosure. This avoids unreliable dosing with the container being nearly empty.

In other embodiments, the counter is arranged to be incremented by displacement of the spout. Normally such a counter will be a mechanical counter including a rotatable member indexed by one increment on each displacement of the spout.

Such a mechanical counter can include a dual set of ratchet teeth and pawls, one of either of the teeth and the pawls being displaced with the spout the other being fast with the outer enclosure and the rotatable member being incremented partially by one of the dual set of teeth on inwards displacement of the spout and partially by the other of the dual set of teeth on return outwards displacement of the spout.

Alternatively, the mechanical counter can include a single set of ratchet teeth and at least one pawl and a frictional member restraining the rotatable member, one of either of the teeth and the pawls being displaced with the spout the other being fast with the outer enclosure and the rotatable member being incremented by the pawl and teeth on inwards displacement of the spout and held by the frictional member on return outwards displacement of the spout.

In one of these embodiments:
the rotatable member is a portion of the inner pressurised container or a sleeve fast with the container, the container or the sleeve being adapted to be indexed by one increment on each displacement of the spout,
the said portion or sleeve has a helical track,
the window extends axially and/or circumferentially of the outer enclosure and
the source includes an indicator adapted to co-operate with the helical track for indicating movement along the extent of the window.

Alternatively:
the rotatable member is a member internal of the outer enclosure, extending around the inner container and having a helical track,
the window extends axially and/or circumferentially of the outer enclosure and
the source includes an indicator adapted to co-operate with the helical track for indicating movement along the extent of the window.

In this alternative, the indicator can have:
a curved inner face engaging the rotatable member, both at the track for movement of the indicator and laterally for location of the indicator and
a flat outer face engaging the window with lateral extent for locating the indicator in the window circumferentially of the outer enclosure.

Again the indicator can have:
a plain inner face engaging the helical track,
a sprung outer face engaging the window and
sides for locating the indicator in the window circumferentially of outer enclosure and
the window is provided at a groove with sides co-operating with the sides of the indicator in locating the indicator circumferentially of the outer enclosure.

Thirdly, the indicator and the outer enclosure can have a complementary non-circular cross-section for locating the indicator in the window circumferentially of the outer enclosure.

It is possible for one of the sets of teeth and pawl(s) or the frictional member, whichever is provided, is arranged at the end of the inner member having the helical track remote from the spout and co-operates with the end of the outer enclosure on incrementing of the inner member. However, usually, both sets of teeth and pawls are provided at the spout end of the outer enclosure.

The member having the helical track can essentially comprise the helical track along the extent of the track and around the inner container and is resilient for movement of its spout end with the spout. However, usually, the member having the helical track comprises a circular cylindrical member around the inner container. The helical track itself can be a channel or groove in the cylindrical member. Alternatively, the helical track can be a rib or ridge on the cylindrical member.

In another feature, the member having the helical track, the indicator and the window are all adapted for plunging movement of the member and the indicator with the spout, a return spring being provided for return movement on outwards movement of the member and indicator after inwards, dispensing movement. Alternatively, the member having the helical track is axially located with respect to the outer enclosure and a separate member plungeable with respect to the outer enclosure is provided, the plungeable member being adapted for driving the helical track member in rotation.

Preferably, wherein the plungeable member is provided with:
means for irrotationally locating it with respect to the outer enclosure and
ones of the pawls or the teeth for rotationally driving the helical track member, the others of the teeth or the pawls being provided on the helical track member.

In this case, the pawls can be resilient axially of the helical track member for return of the plungeable member.

Alternatively the plungeable member can be provided with:
the ones of the pawls or the teeth for rotationally driving the plungeable member, the outer enclosure being provided with the others of the teeth or the pawls,
a plungeable connection with the helical track member for rotation thereof and
a return spring for return movement of the plungeable member on outwards movement of the spout after inwards, dispensing movement.

Again, the helix of the helical track can be regular. Alternatively the helix of the helical track can be less steep in its portion occupied by the indicator on initial use of the source and steeper in its portion indicating imminent exhaustion of the source.

In accordance with an importance feature, the source includes an end cap of the outer enclosure at its end remote from the spout, the end cap being connected to an outer sleeve of the enclosure, at a position such that dispensing operation of the spout and incrementing operation of the counter are synchronised.

In accordance with a second aspect of the invention there is provided a source of a gaseous, gas borne or droplet substance an inner subassembly and an outer subassembly,
the inner subassembly having:
an inner pressurised container,
a substance-release valve device sealed across an end of the container,
a spout displaceable inwards of the container against a spring of the valve device for substance release,
the inner subassembly having an overall length from the distal end of the spout to the remote end of the container, which length decreases on substance release and having at least:
a first quiescent length and
a second length at which the valve is opened for substance release;
the outer subassembly having:
an outer enclosure at least partially enclosing the inner container along its length,
an enclosure cap across the end of the enclosure remote from the spout and at least partially at its spout end, the enclosure cap and the inner container being arranged to react force for displacement of the spout on substance release;
a counter accommodated within the outer enclosure for counting substance release displacements of the spout; and
a counter actuation member arranged beside the spout for displacement inwards to increment the counter
the outer subassembly having an overall length from the actuation member at the spout to a pressurised-container reaction surface, which length decreases on substance release and having at least:
a first quiescent length and
a second length at which counter incrementation is initiated,
the subassembly also having:
a tolerance adjusted connection of the cap to the outer enclosure set with respect to a use installation of the source, whereby the stroke between the first and second lengths of the respective assemblies is compensated for synchronisation of substance release and count incrementation.

According to a third aspect of the invention, there is provided a dispenser for a gaseous, gas borne or droplet substance, the dispenser comprising:
a source of the first or second aspect;
a mouth piece in connected to the outer enclosure;
a junction member receiving the spout of the source;
a nozzle connected to the junction member and arranged to direct a dose of the substance out through the mouth piece; and
means for actuating the dispenser to dispense the dose and increment the counter.

Normally the valve mechanism will be a metered dose valve mechanism.

DRAWINGS

To help understanding of the invention, a specific embodiment thereof will now be described by way of example and with reference to the accompanying drawings, in which:

FIG. 3 is a view similar to FIG. 1 of a second source of the invention;

FIG. 4 is a top view of the source of FIG. 3;

FIRST PREFERRED EMBODIMENT

Figure 1:
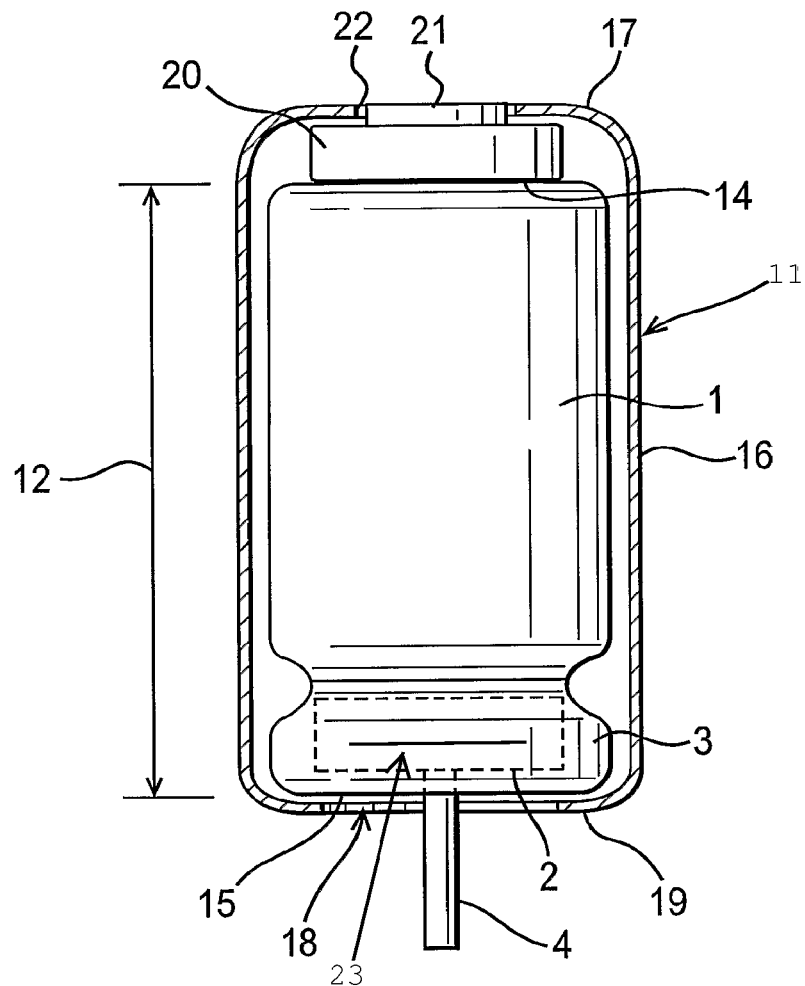
FIG. 1 is a partially sectioned side view of a first medicament source according to the invention.
Figure 2:
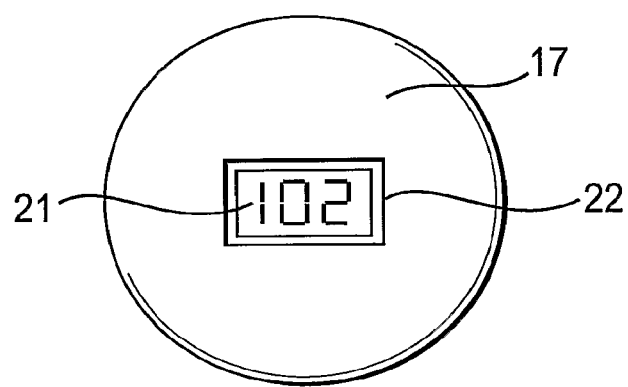
FIG. 2 is a top end view of the source of FIG. 1.
Figure 5:
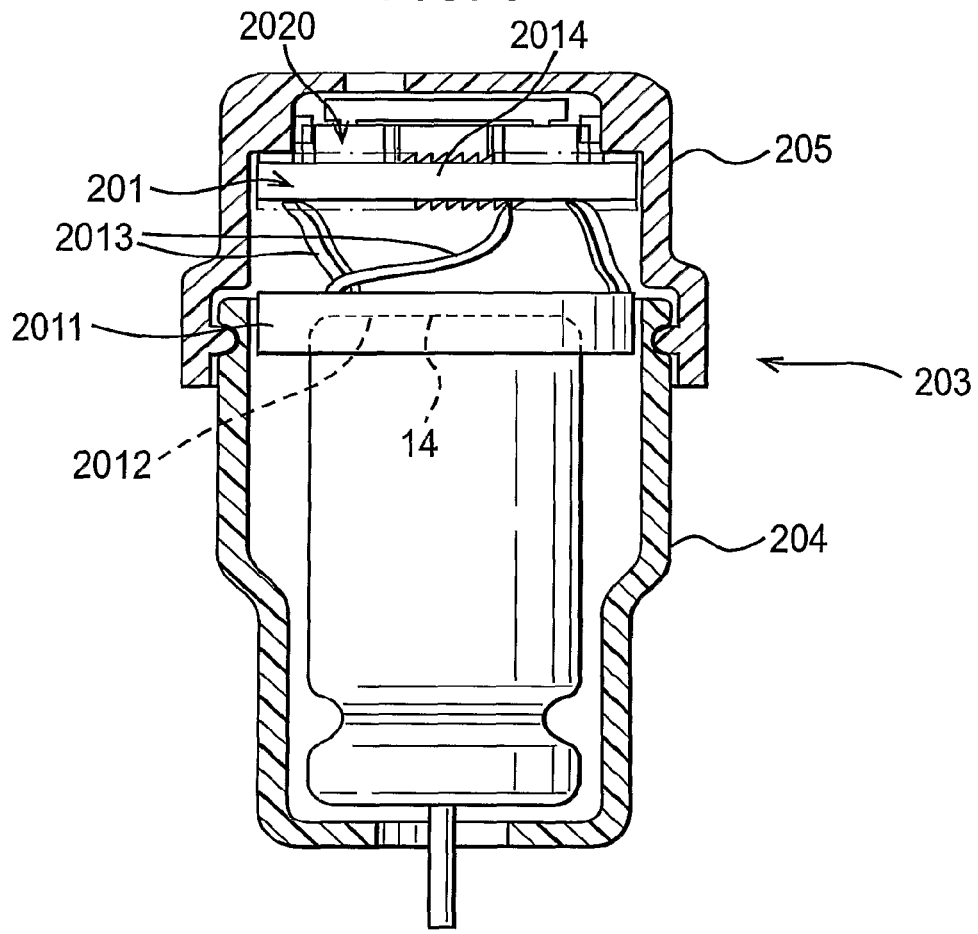
FIG. 5 is a side view of a third source of the invention.
Figure 6:
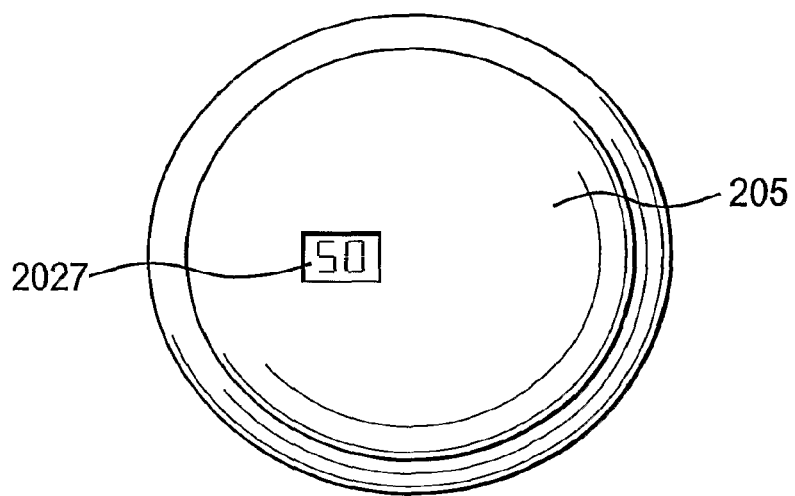
FIG. 6 is a top view of the source of FIG. 4.
Figure 7:
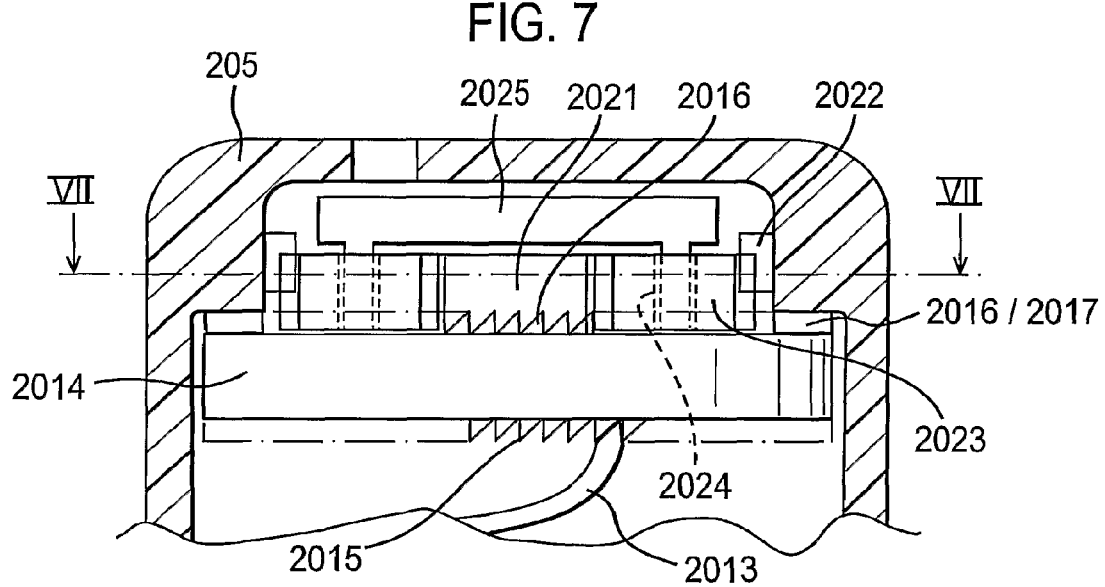
FIG. 7 is a more detailed view of the mechanical counter of the third source.
Figure 8:
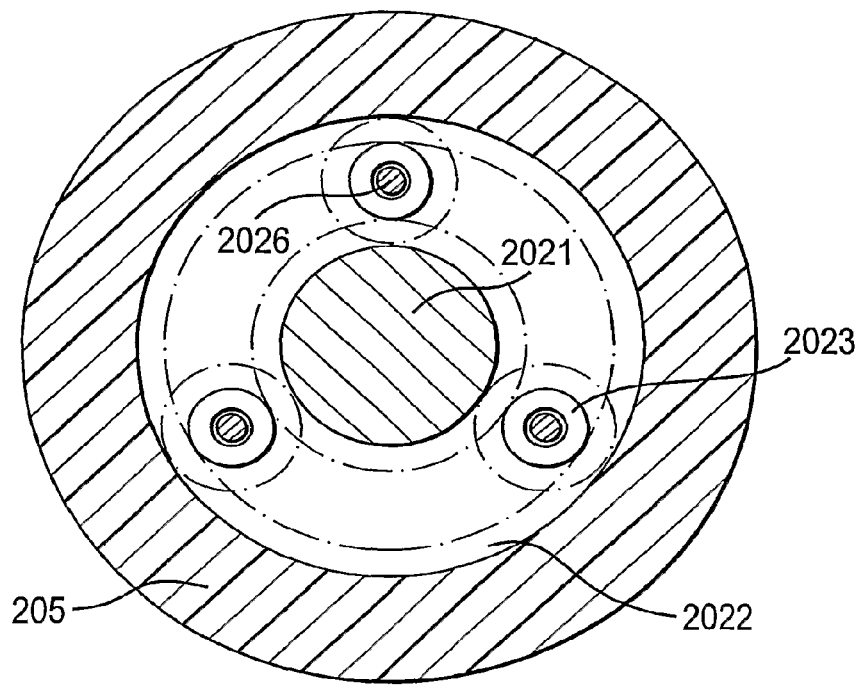
FIG. 8 is a s sectional view on the line VII-VII in FIG. 7 of the epicyclic gearbox of the counter of FIG. 7.

In the first embodiment, the medicament source shown in FIGS. 1 & 2 has:
- an inner pressurised container 1 of stamped aluminium,
- a substance-release valve device 2 sealed across an end of the container by means of a crimp cap 3,
- a spout 4 displaceable inwards of the container against a spring 23 of the valve device for release substance.

These features are conventional.

In accordance with the invention, the source also includes an outer sleeve 11 enclosing the inner container along its length 12, across its end 14 remote from the spout and at least partially at its spout end 15. In this embodiment, the sleeve also is of stamped aluminium, with a circularly cylindrical body 16, a closed end 17 and an open end 18 at which it has a turned-in rim 19, captivating the imler container in the outer sleeve by engagement under the crimp cap. Only the spout 4 extends from the outer sleeve.

Between the end 14 of the inner container opposite from the spout 4 and the end 17 of the outer sleeve is accommodated an electronic counter 20, of the type which increments or more precisely decrements each time a compressive force is applied across it. The counter per se is of a known type. It has a display 21 aligned with a window 22 in the end 17 of the outer sleeve.

In use, with the spout received in the junction member of an inhaler body (not shown), pressure on the end 17 of the outer sleeve urges it and the inner container down, with the spout being pushed inwards and causing the valve to release a dose through the junction member.

The force to actuate the valve is transmitted from the outer sleeve to the inner container via the counter, which decrements its display. Thus the user can monitor how many doses remain in the source by viewing the display through the window 22.

SECOND EMBODIMENT

Turning now to a second embodiment shown in FIGS. 3 & 4, whilst the previous embodiment is suitable for high value medicaments, it is not suitable for low value medicaments where the counter may be the most expensive component including the medicament. In this embodiment, the counter 101 is removable and equipped with a switch 102 which turns on the counter only when pressed in and resets the counter in doing so.

Whereas the outer sleeve 103 of the first embodiment is of aluminium, that of the second embodiment is a two part plastics material moulding, suitably of polypropylene. It comprises a sleeve component 104 and an end cap component 105. They have complementary formations 106, 107 for clipping the cap onto the sleeve. The latter is circularly cylindrical, with a turned in lower rim 108 and internal formations 109 for clipping into the crimp neck 6 of the inner container, which is identical to that of the first embodiment—hence use of the same reference numerals in this respect. The formations discourage removal of the sleeve, but are provided with clearance from the crimp neck, whereby actuation for medicament dispensing always results in dispensing force application to the sleeve via the counter 101. The sleeve is of sufficient length to discourage use of the source without the cap 105 fitted, in that the end 14 of the inner container is not readily accessible through the open end of the sleeve.

With a counter 101 fitted in the open end and the cap 105 fitted, the end 14 of the inner container abuts against the counter and the counter abuts against the cap, at least on pressure on the cap for use of the source. Fitting of the counter and cap has switched on the counter, whose display is visible through a window 110 in the cap. Pressing on the cap 105 or indeed the counter via its window results in (1) force being transmitted to the inner container for valve actuation and dose dispensing and (2) the dispensing act being counted.

The sleeve formation 106 has a groove on the outer surface of the sleeve and the cap formation 107 has an inwards-facing rim on tear-off, annular strip 111. When the source is exhausted, the strip is torn off, the counter removed for use with a new source and the rest of the source is discarded.

THIRD EMBODIMENT

Turning now a third embodiment, shown in FIGS. 5 to 8, the outer sleeve 203 is also a two part component, comprising a sleeve part 204 and a cap which is longer to accommodate a mechanical counter 201, which is deeper than its electronic counterpart. It has an inner-container engagement member 2011, with a recess 2012 for tightly receiving the container end 14 and three resilient pawl members 2013 which curve shallowly curve around and away from the spout. They engage a rotary ratchet member 2014 with oppositely directed ratchet teeth 2015, 2016 on its bottom and top faces. The teeth 2015 are complementary to the pawl members 2013, whilst the teeth 2016 are complementary to rigid pawl teeth 2017 on the cap 205. It is anticipate that that the member 2011 will be held against rotation by the spout 4 of the container 1; however, if need be it can be splined to the sleeve part 204. Dispensing of a dose causes the pawl members to drive the ratchet member around with the teeth 2016, 2017 riding over each other by one pitch. On release of the dispensing force, the pawl members maintain the engagement of the teeth 2016, 2017 in their new position.

To allow a count of 200 doses requires a circle of 200 ratchet teeth. This is difficult to achieve with an inner container of 23 mm, a typical size, since the pitch of the teeth is:

$$23 \times 3.14/200 = 0.36 \text{ mm}.$$

In this embodiment the teeth are set at a greater pitch, but there are less of them. Their effect is modified by an epicyclic gearbox 2020. This comprises a sun wheel 2021 integral with the ratchet member 2014. It is arranged within an annular gear 2022 moulded integrally with the cap 205, with its teeth set inwards from the upper ratchet teeth 2016. Three planet wheels 2023 having central bores 2024 are arranged between the sun wheel and the annular wheel. As the ratchet member and with it the sun wheel is ratcheted around, the planet wheels roll around with it. With a comparatively small sun wheel, several turns of it are required for complete traverse of the planet wheels around the gearbox. A carrier 2025 has pins 2026 which extend down into the bores of the planet wheels. On its top surface, the carrier has graduations visible through a window 2027 in the end cap. Thus the number of doses used/remaining can be determined by viewing the graduations, which successively pass the window.

FOURTH EMBODIMENT

Figure 9:
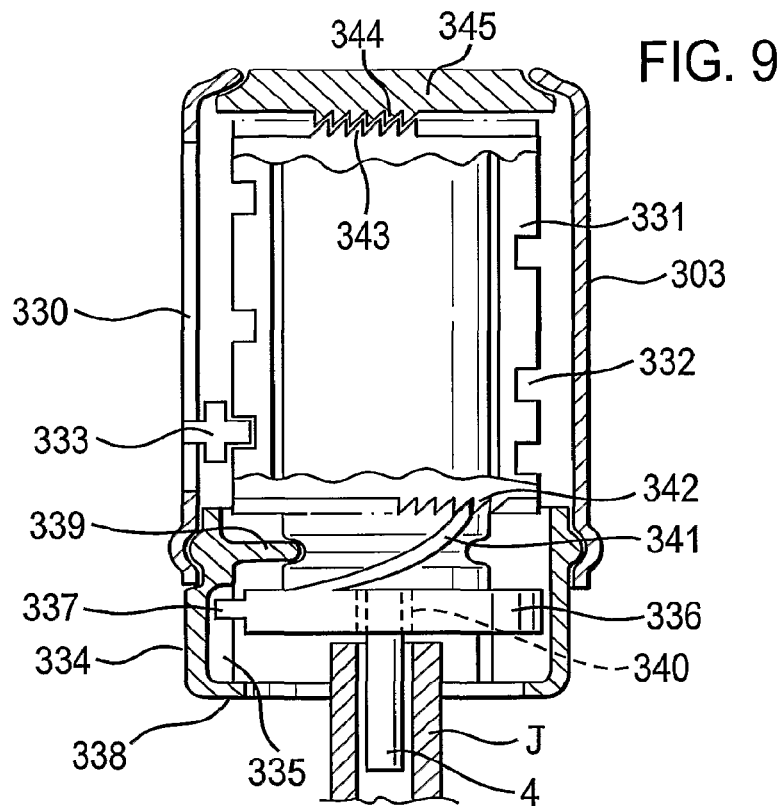
FIG. 9 is side partially sectioned side view of a fourth source of the invention.
Figure 10:
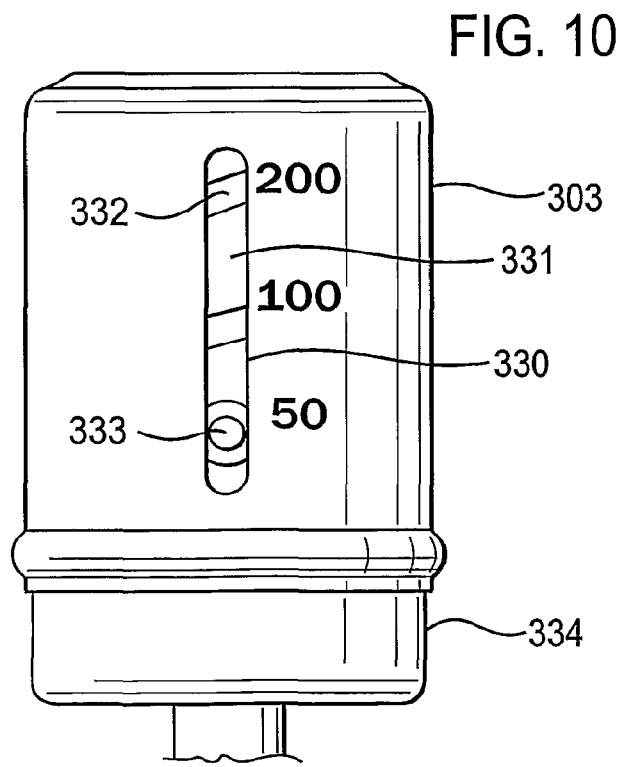
FIG. 10 is a plain side view of the fourth source.

Turning on now to the fourth embodiment of FIGS. 9 and 10, the source there shown has an outer sleeve 303 of aluminium, with a slot 330 extending along the greater part of its length. Immediately within the sleeve is a secondary sleeve 331 with a helical groove 332. An indicator 333 in the form of a disc with studs on either side engages with its studs in the slot and the groove. Thus as the secondary sleeve is turned, the indicator is moved along the slot. The helix is uneven, being steeper at the spout end of the outer sleeve, where initial doses show only small movement of the indicator, whereas dispensing of the final doses causes faster movement of the indicator.

The secondary sleeve is moved in a manner akin to the ratchet member of the preceding embodiment. At the spout end of the outer sleeve, it is crimped onto a guide member 334 having three short longitudinal grooves 335, which guide a yoke 336, having fingers 337 extending into the grooves. The ends of the grooves are closed 338 to captivate the yoke. The upper ends of the grooves are closed by projections 339 that extend to the crimp cap of the inner container, locating it within the outer sleeve. The yoke has a central bore 340 for the spout 4 and three resilient pawl members 341, which are spaced between the projections 339. The pawl members extend up to engage with teeth 342 provided on the bottom edge of the secondary sleeve. The top edge of this sleeve also has teeth 343, which co-operate with fixed pawl teeth 344 on a cap 345 crimped to the outer sleeve.

In use, the source is mounted in a dispenser body (not shown except for a junction J), with the spout engaged in a junction member. Depression of the source towards the junction member pushes the spout into the valve and the yoke also towards the valve. The flexible pawls 341 are permanently engaged with the lower teeth 342, whatever the position of the yoke, and as the yoke is urged in towards the inner container, the pawls foreshorten, rotating the secondary sleeve. The upper teeth are indexed across the fixed pawl teeth. As the source is allowed to return after dispensing its dose, the resilient pawls continue to urge the secondary sleeve up against the fixed pawls, with the result that the sleeve is held against rotation. The resilient pawls ride over the lower teeth, setting themselves for the next dispensing action. On successive actions, the secondary sleeve moves progressively round, driving the indicator down the slot 330 as described above.

Figure 11:
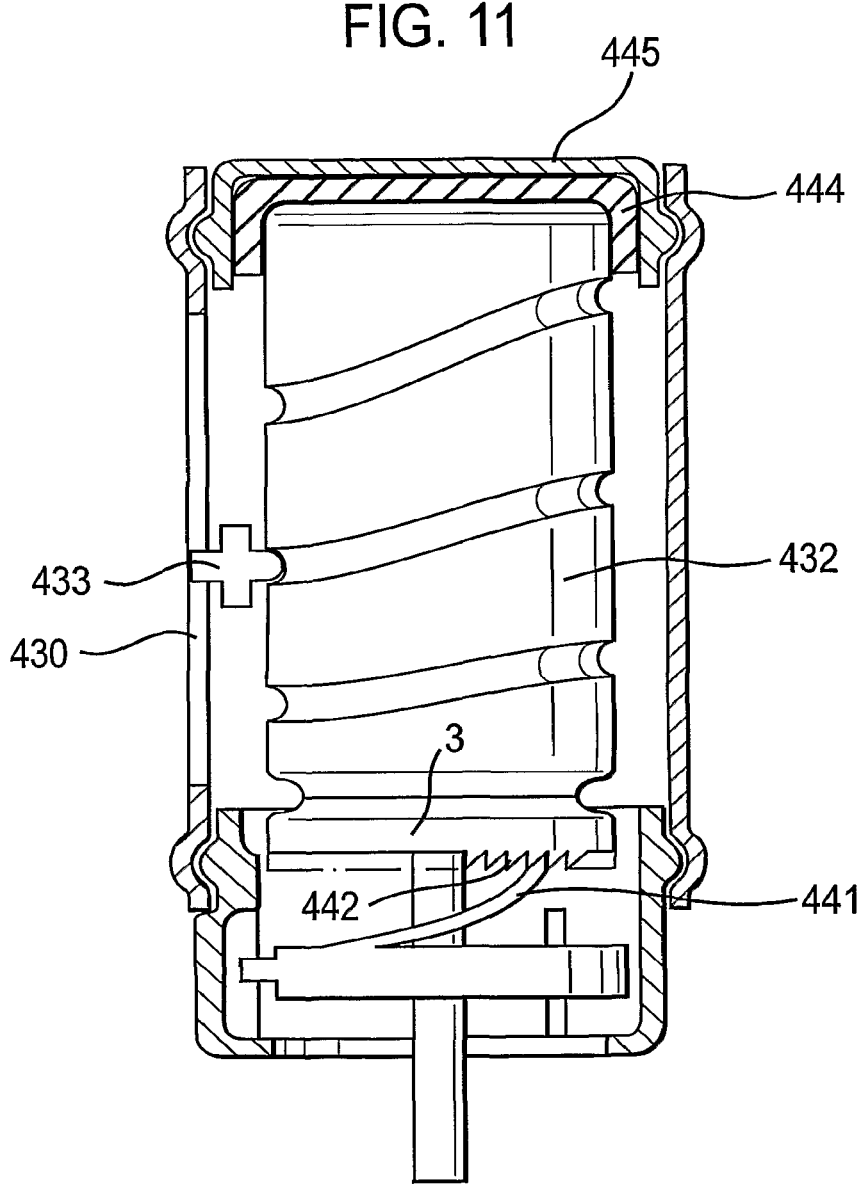
FIG. 11 is a partially sectioned side view of a first variant of the fourth source.

A first variant of the fourth embodiment, as shown in FIG. 11 has distinct similarities to the previous embodiments, save that the function of the helical groove in the secondary sleeve is performed by a helical groove 432 impressed in the wall of the inner container. The function of the upper teeth and the fixed pawls is performed by an elastomeric ring 444 pushed into an outer-sleeve cap 445. Then the function of the lower ratchet teeth is performed by teeth 442 impressed into the crimp cap 3 of the inner container. The resilient pawls 441 act on the teeth 442, progressively rotating the inner container with respect to the outer sleeve and driving an indicator 433 along a slot 430 in the outer sleeve.

Figure 12:
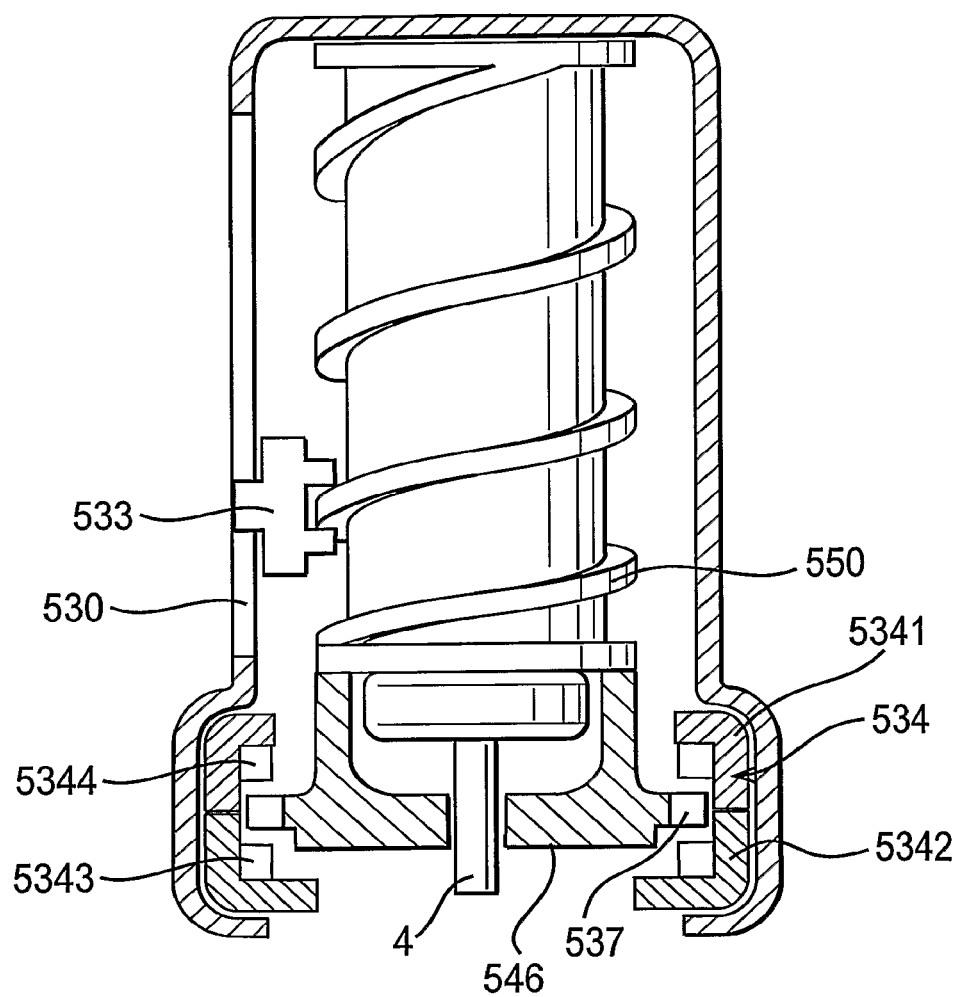
FIG. 12 is a similar view of a second variant of the fourth source.
Figure 13:
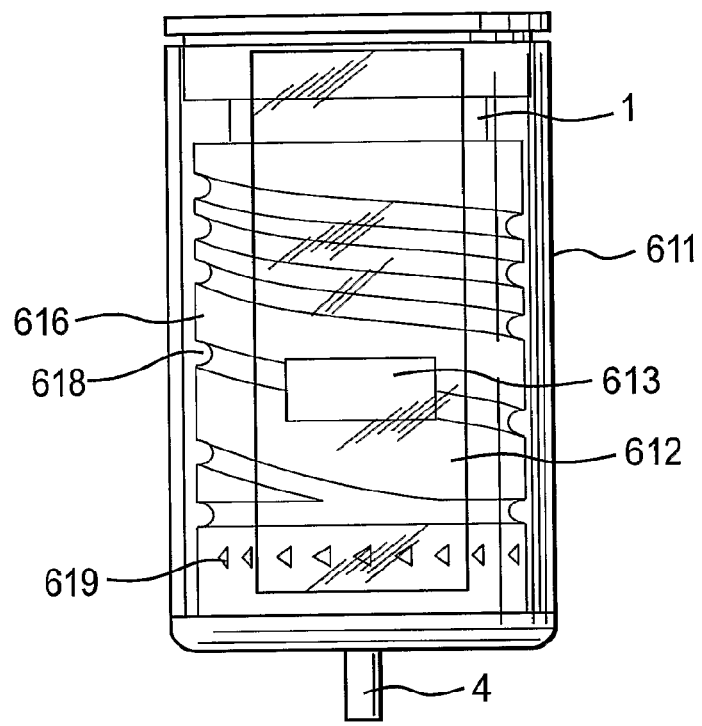
FIG. 13 is a side view of a fifth source of the invention.
Figure 14:
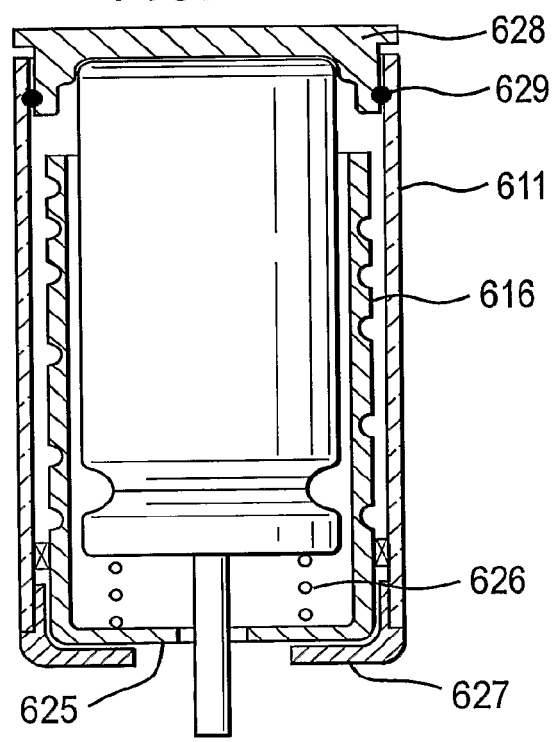
FIG. 14 is a cross-sectional side view of the fifth source.
Figure 15:
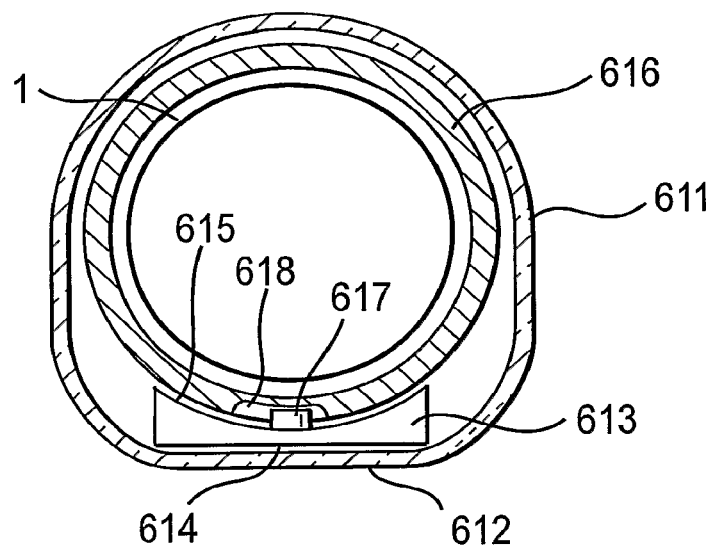
FIG. 15 is a cross-sectional plan view of the fifth source.
Figure 16:
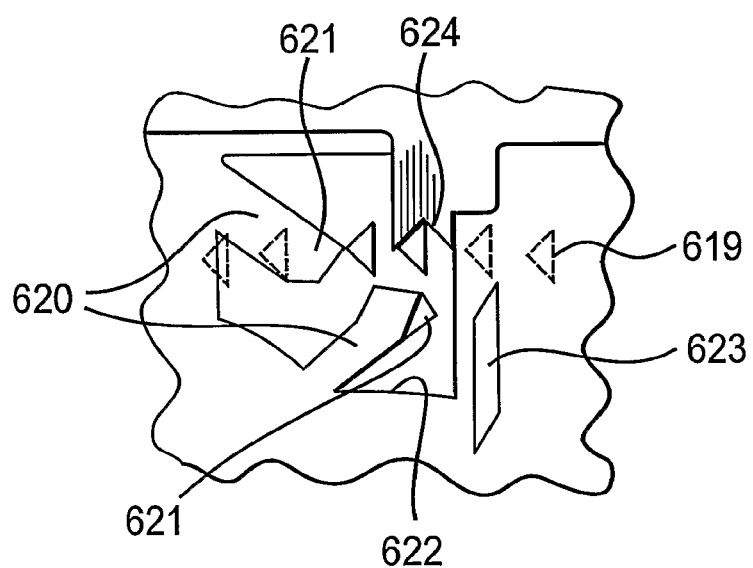
FIG. 16 is a scrap view of the teeth and pawls of the fifth source.

The second variant, shown in FIG. 12, differs in that the yoke 546 is rotatably carried on the spout. The yoke is fast with a helical member 550, which is formed as a progressively tighter winding. It carries an indicator 533, co-operating with a slot 530 in an outer sleeve. The helical member abuts against the closed end of the outer sleeve, to urge the yoke permanently downwards. The outer sleeve is crimped to a two part yoke drive member 534. The two parts 5341,5342 have oppositely directed ratchet teeth 5343,5344, with face each other in positions that would be interdigitated if they were not spaced from each other. The yoke has a set of fingers 537 which are arranged between these teeth.

As the source is depressed and the spout is driven inwards, the yoke is urged inwards against the resilience of the helical member. The fingers 537 slide along the faces of the upper teeth 5341 and rotate the helical member. As the spout is released, the fingers move back and engage the lower teeth 5342, further rotating the helical member. The result is that the fingers come to rest indexed one by one pitch of the upper teeth—and indeed one pitch of the lower teeth—ready for the next depression of the spout.

In a non-illustrated embodiment, the moulded plastics material helix of FIG. 12 can be replaced by a spring wire helix.

FIFTH EMBODIMENT

Turning now to the fifth embodiment, shown in FIGS. 13 to 16, the source there shown has a pressurised container 1, with a spout 4. As shown, the upper part of the container is visible through an outer sleeve 611 of transparent plastics material. This has a flat window 612, through which an indicator 613 can be viewed. The indicator has a flat front face 614, which abuts the flat inside of the window. Rear face 615 of the indicator is curved to match the curvature of a helically grooved inner member 616. The indicator has a rear protrusion 617 into the groove 618. This arrangement not only connects the indicator to the groove, but also prevents the indicator from turning about the protrusion due to the curvature of the rear face. Further, the indicator is restrained from moving along the groove. Such movement would involve the front face 614 moving out of alignment with the window. However, again the curved rear face restrains such movement.

The pitch of the groove 618 is small at the end of the inner member remote from the spout, but increases at the spout end to alert the user that a new source will shortly be required. The arrangement for indexing the inner member 616 is a series of triangular teeth 619 moulded on the inside of the outer sleeve and a pair of oppositely directed flexible pawl arms 620 with pawl elements 621 at their distal end moulded in a cut out 622 in the inner member. A rigid pawl member 623 and a rigid locator notch 624 are provided. In use, the pawl element on the spout side of the teeth 619 makes initial contact with a tooth, followed by contact by the pawl 623 with the neighbouring tooth. Continued movement of the inner brings a parallel portion of the rigid pawl between these two teeth. One return movement, the other flexible pawl continues the indexing movement which is completed by the next tooth coming to rest in the notch 624. This movement is initiated by a junction member, not shown, in which the spout 4 is received, abutting an in-turned rim 625 of the inner member, whereby depression of the container 1 and with it the outer sleeve 611 and its teeth 619 releases a dose from the spout and performs the first part of the indexing as described. A return spring 626 is provided between the rim 625 and the crimp cap 3 of the container.

Other details of the source are that outer sleeve has a clipped on rim 627 outside the inner rim 625 at the spout end. Further the sleeve has an end cap 628 welded on at 629 to close the other end of the sleeve and locate the container axially with respect to the sleeve. The relative position of the container and the sleeve are important, because the spout co-operates with elastomeric parts, the tolerance of whose position with respect to the cap 3 and the body of the container 1 is not tight. The result is the possibility of the release of the dose not being synchronised with the incrementing of the counter. In other words either may occur without the other. This can be avoided by arranging the relative quiescent position of the spout and the rim such that on inwards movement of the stem to its release position, the inner member is stroked to its indexing position. This is achieved by (1) measuring the overall length of the container and spout in quiescent state from the spout's distal end to the container's remote end and (2) welding the end cap 628 to the sleeve with a consequently determined length between the outer face of the rim 625 and outer face of the end cap with the rim not yet fitted. The result is that with the spring 626 holding the container 1 against the end cap 628 and the inner member against the teeth 619, both at the notch 624 and other corresponding abutments 630 around the member 616, the spout protrudes with a determined amount from the rim 625. Synchronisation of dose release and indexing are thus achieved.

SIXTH EMBODIMENT

Figure 17:
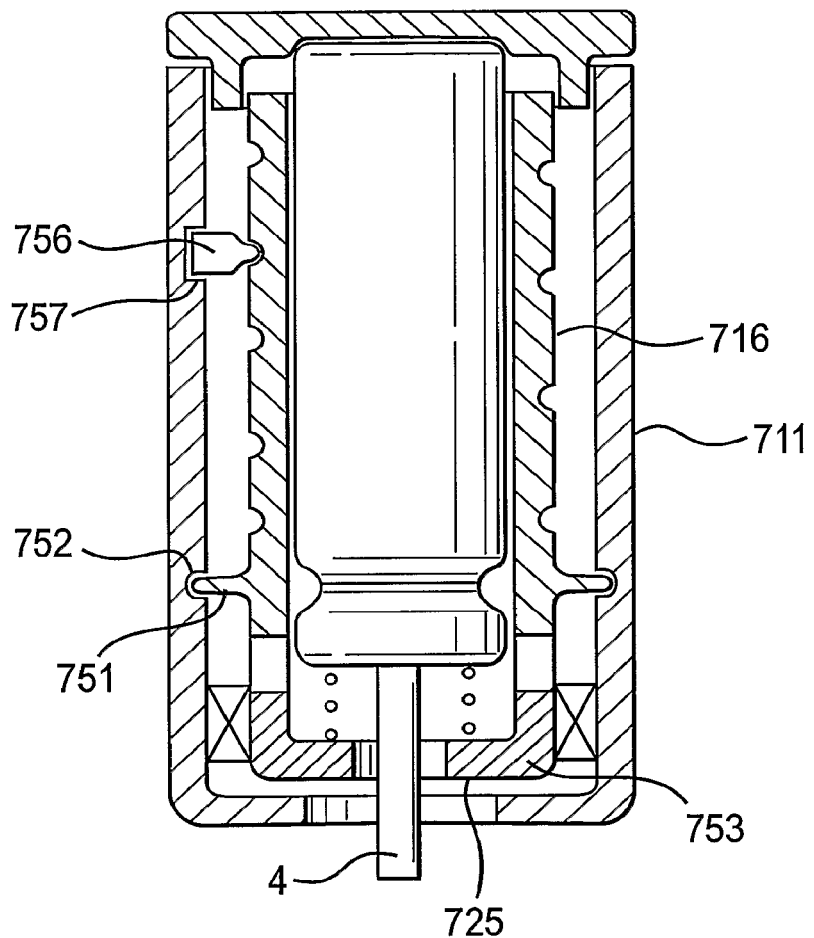
FIG. 17 is a cross-sectional side view of a sixth source.
Figure 18:
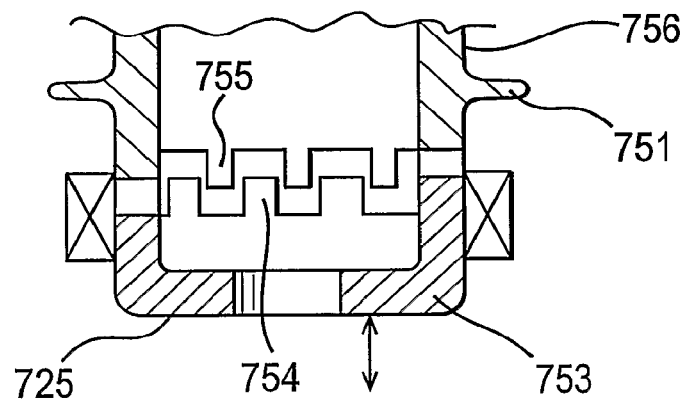
FIG. 18 is a scrap view of a plunging connection the sixth source.
Figure 19:
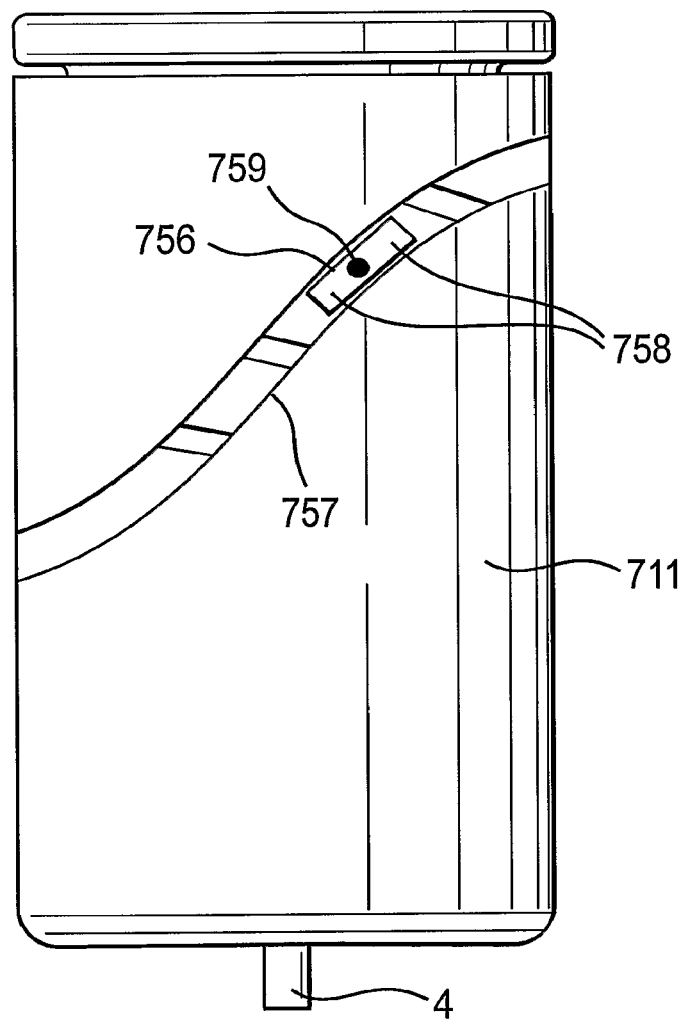
FIG. 19 is a side view of the sixth source.

The sixth embodiment of FIGS. 17 to 19 differs in a few but significant details. Its inner member 716 is axially located with respect to the outer sleeve 711 by means of a bead 751 on the inner member engaging in a groove 752 in the outer sleeve. A plunging extension 753 of the inner member, having its rim 725 with the spout 4 passing through it and the inner members pawls (not shown), has fingers 754 in plunging mesh with fingers 755 on the inner member 716. Thus dispensing action plunges the extension 753 only with respect to the outer sleeve 711 without plunging of the marker as occurs in the fifth embodiment.

The marker 756 is guided in a helical channel 757 extending both along and around the outer sleeve, providing enhanced opportunity of accurate graduation (not shown). It has a pip (not shown) on its back side and two fingers 758, which are resilient a extend outwards when free, which urge the marker into engagement with the helical channel. It has a central mark 759

SEVENTH EMBODIMENT

Figure 20:
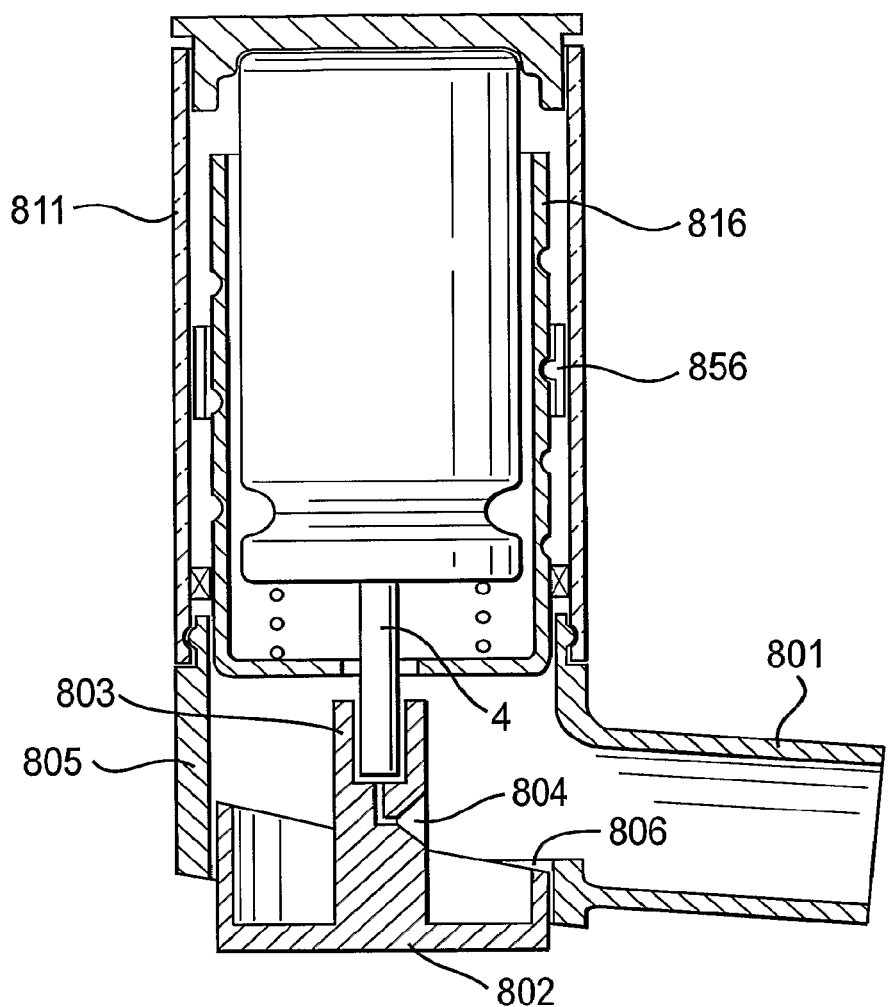
FIG. 20 is a cross-sectional side view of a dispenser of the invention incorporating a source of the disclosure.
Figure 21:
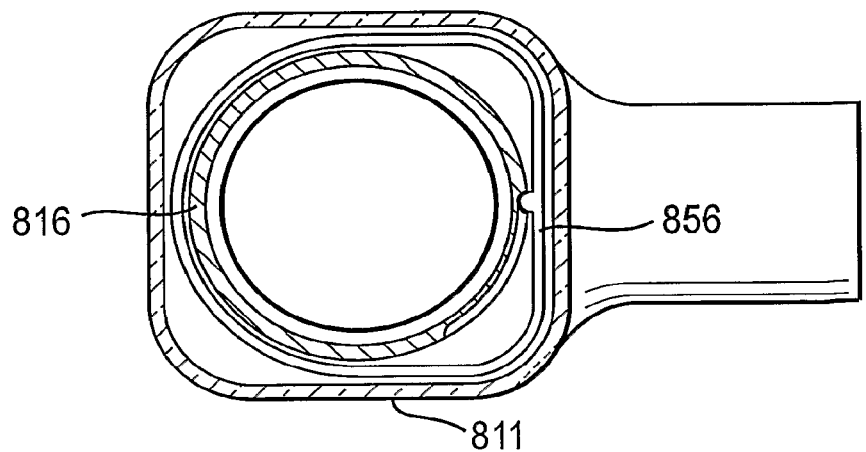
FIG. 21 is a cross-sectional plan view of the dispenser of FIG. 20.

The seventh embodiment of FIGS. 20 & 21 differs in that the source integrally includes a mouthpiece 801 and an actuation button 802, including a junction 803 receiving the spout 4 and having a nozzle 804 directed out of the mouth piece. FIG. 20 is a cross-sectional side view of a dispenser of the invention, including elements 801, 802, 803, 804, 811, 816 and 856, incorporating a source of the disclosure.

The mouthpiece is moulded in a piece 805 fitted in place of the clipped on rim 627 of the fifth embodiment. The moulding 805 has an aperture 806 in which the button 802 is received.

A further difference is that whilst the inner member 816 is circularly cylindrical, the outer sleeve 811 is non-circular. The marker 856 is formed as a stirrup around the inner member and is restrained from moving around it by having a shape complementary to the outer sleeve.

I claim:

1. A container of a gaseous, gas borne or droplet substance having:
   an inner pressurised container for the substance,
   a substance-release valve device sealed across an end of the inner pressurized container and having a spring,
   a spout at a spout end of the inner pressurized container, which is displaceable inwards of the inner pressurized container against the spring of the valve device for substance release,
   the container also including:
   an outer enclosure enclosing the inner pressurized container along its length, at least partially across its end remote from the spout and partially at its spout end, the outer enclosure and the inner pressurized container being arranged to be capable of reacting to cause displacement of the spout inwards of the inner pressurized container for substance release;
   a mechanical counter accommodated within the outer enclosure for counting substance release displacements of the spout, wherein the counter is arranged to be incremented on displacement of the spout, and the counter includes a rotatable member indexed by one increment on each displacement of the spout,
   wherein the rotatable member is a portion of the inner pressurised container or a sleeve fast with the container, the container or the sleeve being adapted to be indexed by one increment on each displacement of the spout, or the rotatable member is a member internal of the outer enclosure, extending around the inner pressurized container, the rotatable member having a helical track;
   a window in the outer enclosure for viewing the count of the counter extending axially and/or circumferentially of the outer enclosure; and
   an indicator adapted to co-operate with the helical track which operates as an indicator by movement along the window.

2. A container as claimed in claim 1, wherein the counter is arranged at an end of the outer enclosure, for transmitting spout-displacement force between the inner container and the outer enclosure and counting occurrences of such force.

3. A container as claimed in claim 2, wherein the counter is a removable or irremovable mechanical counter.

4. A container as claimed in claim 1, wherein the mechanical counter includes a dual set of ratchet teeth and pawls, with angular incrementation determined by the ratchet teeth.

5. A container as claimed in claim 4, wherein the mechanical counter includes a dual set of ratchet teeth and pawls, one of either of the teeth and the pawls being displaced with the spout the other being fast with the outer enclosure and the rotatable member being incremented partially by one of the dual set of teeth on inwards displacement of the spout and partially by the other of the dual set of teeth on return outwards displacement of the spout, or
   a single set of ratchet teeth and at least one pawl and a frictional member restraining the rotatable member, one of either of the teeth and the pawls being displaced with the spout the other being fast with the outer enclosure and the rotatable member being incremented by the pawl and teeth on inwards displacement of the spout and held by the frictional member on return outwards displacement of the spout.

6. A container as claimed in claim 5, wherein one of the sets of teeth and pawl(s) or the frictional member, whichever is provided, is arranged at the end of the rotatable member having the helical track remote from the spout and cooperates with the end of the outer enclosure on incrementing of the rotatable member.

7. A container as claimed in claim 1, wherein
the rotatable member has a curved surface; and
the indicator:
engages the helical track for movement of the indicator, and has
a curved inner face engaging the rotatable member at the helical track for location of the indicator circumferentially of the rotatable member, and
a flat outer face engaging the window for locating the indicator at the window circumferentially of the outer enclosure.

8. A container as claimed in claim 1, wherein the indicator and the outer enclosure have a complementary non-circular cross-section for locating the indicator in the window circumferentially of the outer enclosure.

9. A container as claimed in claim 1, wherein the rotatable member having the helical track comprises a circular cylindrical member around the inner pressurized container and the helical track is a channel or groove in the cylindrical member or a rib or ridge on the cylindrical member.

10. A container as claimed in claim 9, wherein the rotatable member having the helical track, the indicator and the window are all adapted for plunging movement of the member and the indicator with the spout, a return spring being provided for return movement on outwards movement of the member and indicator after inwards, dispensing movement.

11. A container as claimed in claim 10, wherein the rotatable member having the helical track, the rotatable member having the helical track is axially located with respect to the outer enclosure and a separate member plungeable with respect to the outer enclosure is provided, the plungeable member being adapted for driving the helical track member in rotation.

12. A container as claimed in claim 9, wherein the plungeable member is provided
with:
means for irrotationally locating it with respect to the outer enclosure; and
pawls or teeth for rotationally driving the rotatable member;
cooperating teeth or pawls respectively being provided on the rotatable member having the helical track.

13. A container as claimed in claim 1, wherein the helix of the helical track is regular, or the helix of the helical track is less steep in its portion occupied by the indicator on initial use of the source and steeper in its portion indicating imminent exhaustion of the container.

14. A container as claimed in claim 1, including an end cap of the outer enclosure at its end remote from the spout, the end cap being connected to an outer sleeve of the enclosure, at a position such that dispensing operation of the spout and incrementing operation of the counter are synchronised.

* * * * *